(12) United States Patent
Cunningham et al.

(10) Patent No.: US 6,558,383 B2
(45) Date of Patent: May 6, 2003

(54) INERT GAS INHANCED ELECTROSURGICAL APPARATUS

(75) Inventors: James Steven Cunningham, Boulder, CO (US); Paul Ray Romero, Loveland, CO (US)

(73) Assignee: Sherwood Services AG, Schaffhausen (CH)

( * ) Notice: Subject to any disclaimer, the term of this patent is extended or adjusted under 35 U.S.C. 154(b) by 10 days.

(21) Appl. No.: 09/974,610

(22) Filed: Oct. 10, 2001

(65) Prior Publication Data

US 2002/0022838 A1 Feb. 21, 2002

Related U.S. Application Data

(63) Continuation of application No. 09/504,640, filed on Feb. 16, 2000.

(51) Int. Cl.[7] .................................................. A61B 18/18
(52) U.S. Cl. .......................................... 606/41; 606/49
(58) Field of Search ....................................... 606/41–50

(56) References Cited

U.S. PATENT DOCUMENTS

| | | | |
|---|---|---|---|
| 3,903,891 A | | 9/1975 | Brayshaw |
| 4,014,343 A | * | 3/1977 | Esty |
| 4,060,088 A | | 11/1977 | Morrison, Jr. et al. |
| 4,311,145 A | * | 1/1982 | Esty et al. |
| 4,545,375 A | * | 10/1985 | Cline |
| 4,711,238 A | * | 12/1987 | Cunningham |
| 4,901,719 A | * | 2/1990 | Trenconsky et al. .......... 606/49 |
| 5,061,768 A | | 10/1991 | Kishimoto et al. |
| 5,195,959 A | * | 3/1993 | Smith ........................... 604/34 |
| 5,306,238 A | | 4/1994 | Fleenor |
| 5,836,944 A | | 11/1998 | Cosmescu |
| 5,972,416 A | | 10/1999 | Reimels et al. |

* cited by examiner

Primary Examiner—Roy D. Gibson

(57) ABSTRACT

An inert gas enhanced electrosurgical apparatus is disclosed including a housing having at least one ridge formed therein. An electrode assembly has at least a portion thereof disposed within the housing. A support member has at least a portion thereof disposed within the housing and about at least a portion of the electrode assembly. The ridges of the housing are engageable with the support member such that a seal is formed therebetween. The housing can include a first opening adjacent a distal portion of the housing and a second opening adjacent a proximal portion of the housing. Ribs may be formed on an inner surface of the housing. An electrical spring contact may be disposed within the housing and configured to cooperate with the ribs to facilitate electrical communication with the electrode assembly. Wedge projections may be disposed on an outer surface of the housing. The electrode assembly can include an adjustment assembly coaxially disposed about an outer surface of the electrode assembly including a neck member that engages the wedge projections of the housing for incrementally adjusting an amount of movement of the electrode assembly relative to the housing. The support member may include a shroud and an attachment portion. The seal may comprise an O ring seal formed about the shroud.

34 Claims, 8 Drawing Sheets

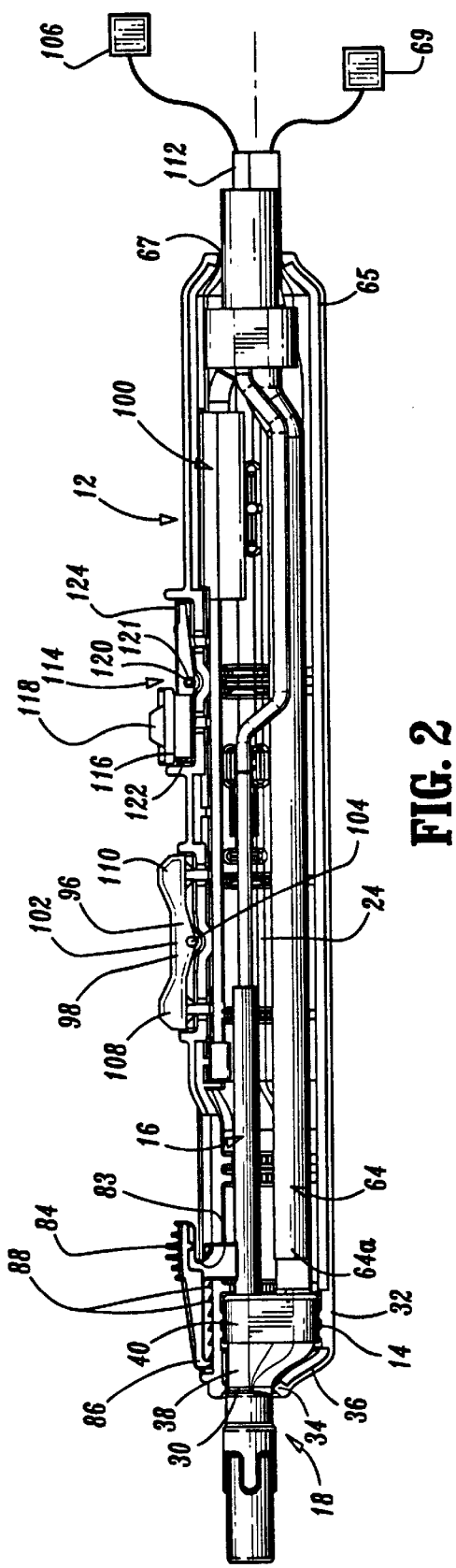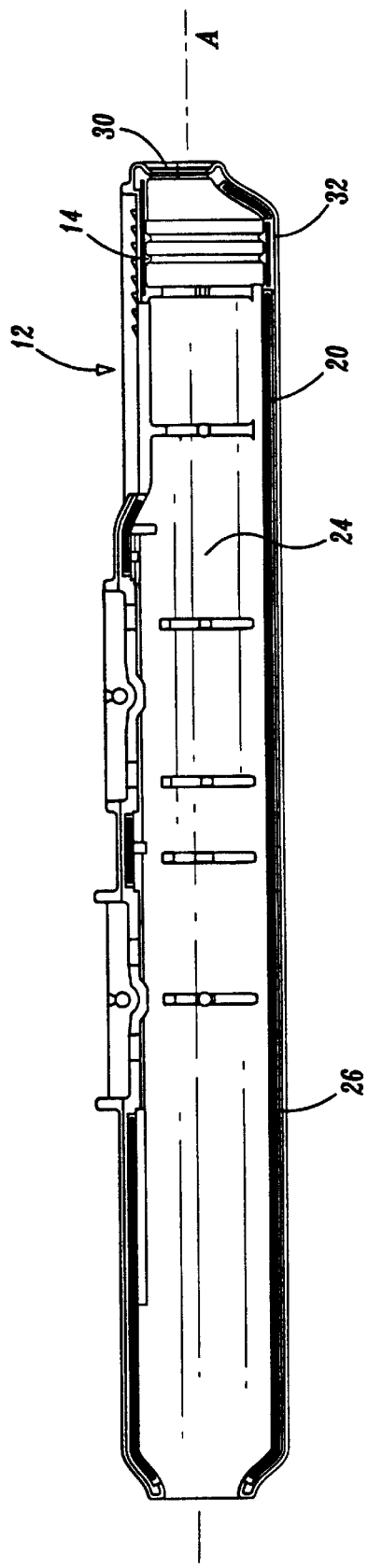
FIG. 2
FIG. 3

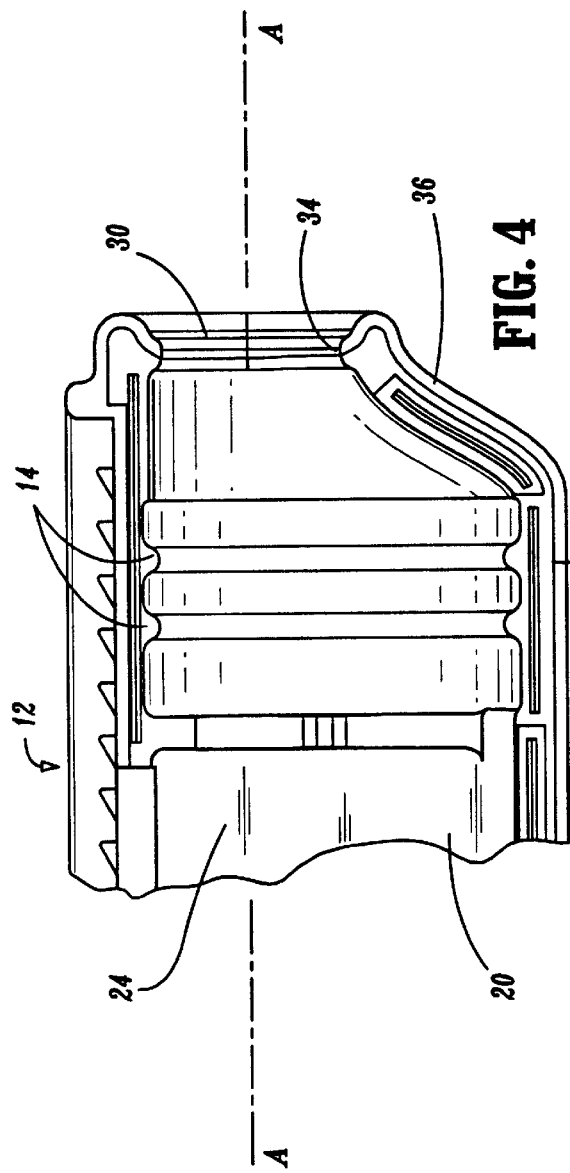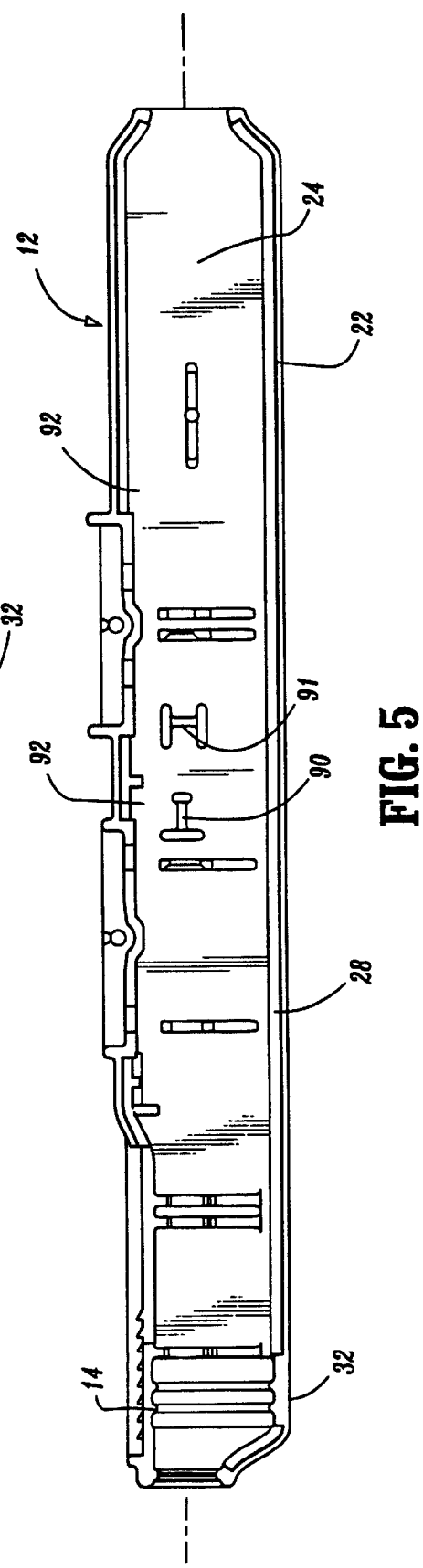

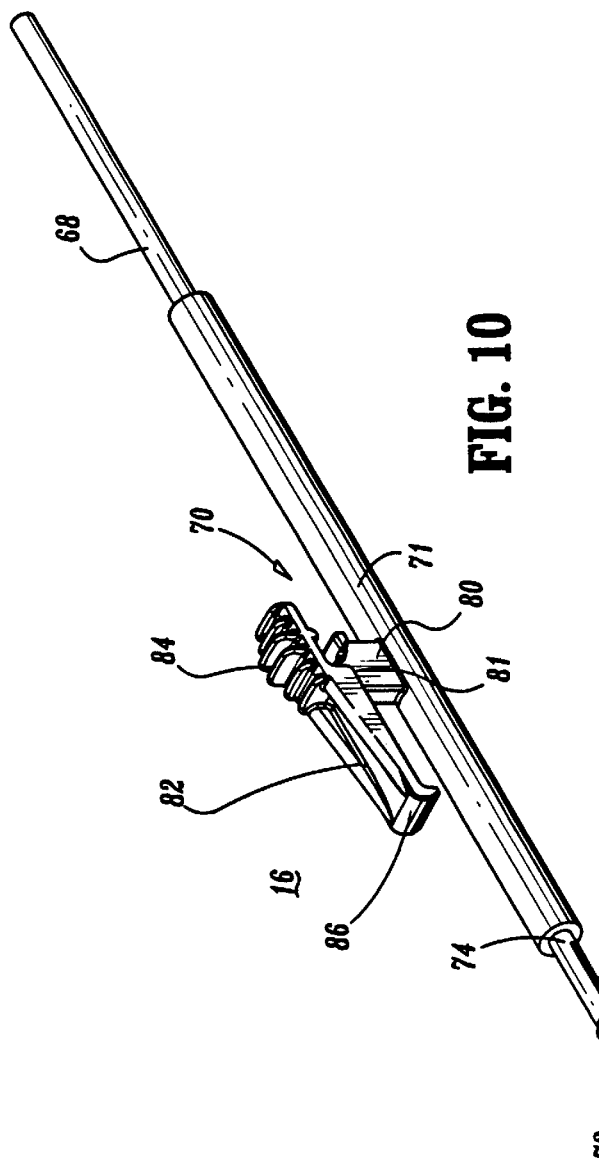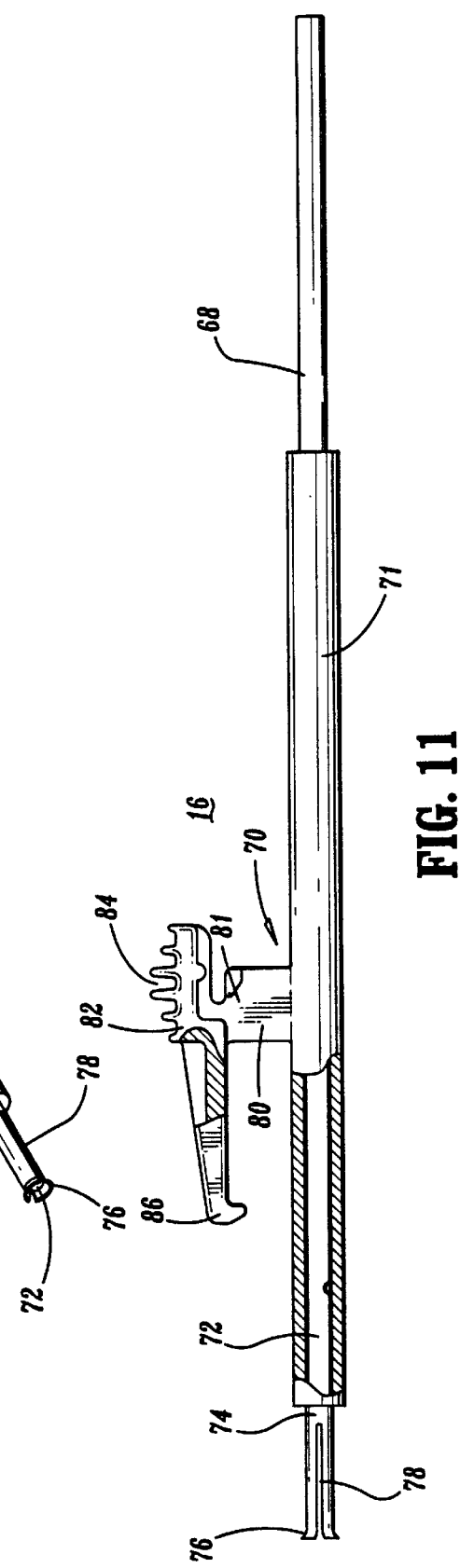

INERT GAS INHANCED ELECTROSURGICAL APPARATUS

This application is a continuation of application Ser. No. 09/504,640, filed Feb. 16, 2000.

BACKGROUND

1. Technical Field

The present disclosure relates generally to apparatus and methods for thermally treating tissue and more particularly, to an inert gas enhanced electrosurgical apparatus for delivering electrosurgical energy.

2. Description of Related Art

Inert gas enhanced electrosurgical devices are effective for cutting, coagulating, desiccating, and/or fulgurating blood or tissue of a patient. These devices create a gas plasma which is ionized and capable of conducting electrical energy to the tissue and bodily fluids. The plasma conducts the energy by providing a pathway of low electrical resistance. An inert gas that is typically used in this manner is argon, however, other inert gases may also be used. A stream of ionized argon, a colorless, odorless, inactive gas, conducts the electrical energy to the tissue and body fluids, while effectively blowing unwanted debris away from a treatment area.

Inert gas enhanced devices used during electrosurgical procedures often employ electrosurgical pencils for transmitting an electric charge to the tissue and/or bodily fluids. Typically, a gas tube is included on the pencil to direct the inert gas from an inert gas source to the pencil. A portion of the gas tube directs the gas for transmitting the electric charge from the pencil.

U.S. Pat. No. 5,061,768 discloses an inert gas electrosurgical pencil connected to an in-line gas filter for directing the gas. Other pencils use a shroud for directing the inert gas whereby the pencil is in a nested engagement with the shroud. U.S. Pat. No. 5,836,944 discloses an electrosurgical pencil with a removable shroud.

The above-mentioned devices may leak the inert gas into and/or about the electrosurgical pencil. Further, many of these devices do not permit adjustment of the electrode for accessing remote areas without the resultant gas leakage discussed above.

Other devices are known whereby an electrode and gas tube are included within the electrosurgical pencil and assembled therein by glue and/or a weld manufacturing process to create a seal about the gas tube and electrode. This type of assembly prevents leakage but disadvantageously adds to the cost of manufacture. Further, a breakdown of the glue and/or weld joint may render the electrosurgical pencil inefficient for electrosurgery.

Therefore, a need exists for an inert gas enhanced electrosurgical apparatus that provides an effective seal about the gas tube and the electrode upon assembly of the electrosurgical apparatus without requiring additional manufacturing processes to form the seal. Further, it would be desirable for the electrosurgical apparatus to provide adjustment of the electrode without impairing the integrity of the seal.

SUMMARY

Accordingly, an inert gas enhanced electrosurgical apparatus is disclosed that provides an effective seal about the gas tube and the electrode upon assembly of the electrosurgical apparatus without requiring additional manufacturing processes to form the seal. Further, the electrosurgical apparatus provides adjustment of the electrode without impairing the integrity of the seal.

In one embodiment, an inert gas enhanced electrosurgical apparatus is disclosed, in accordance with the principles of the present disclosure, which includes a housing having at least one ridge formed therein. Desirably, a plurality of ridges are formed adjacent a distal portion of the housing. The ridges may be oriented substantially orthogonal to a longitudinal axis defined by the housing. An electrode assembly has at least a portion thereof disposed within the housing. A support member has at least a portion thereof disposed within the housing and about at least a portion of the electrode assembly. The ridges of the housing are engageable with the support member such that a seal is formed therebetween. Preferably, a fluid tight seal is formed by an interference fit between the housing and the support member. The support member can be mounted adjacent a distal portion of the housing.

The housing may include a first portion and a second portion that define a cavity therebetween. The first and second portions desirably form interlocking halves. The housing can include a first opening adjacent a distal portion of the housing and a second opening adjacent a proximal portion of the housing. The housing is preferably elongated and tubular.

Alternatively, ribs may be formed on an inner surface of the housing. The ribs may be oriented substantially orthogonal to a longitudinal axis of the housing. The first and the second portions may include ribs. An electrical spring contact is disposed within the housing and configured to cooperate with the ribs to facilitate electrical communication with the electrode assembly.

In an alternate embodiment, wedge projections are disposed on an outer surface of the housing. The electrode assembly includes an adjustment assembly coaxially disposed about an outer surface of the electrode assembly including a neck member that engages the wedge projections of the housing for incrementally adjusting an amount of movement of the electrode assembly relative to the housing. The adjustment assembly facilitates control of the electrically charged stream of inert gas flowing from the electrosurgical apparatus.

In another alternate embodiment, the electrode assembly includes an elongated tubular electrode configured for passage of inert gas thereabout and therethrough a cavity defined therein. The electrode is movably disposed within a cavity of the housing. A distal portion of the electrode may be extendable through the first opening of the housing.

An inert gas activator may be mounted to the housing in communication with an inert gas source. A power source activator can be mounted to the housing and in electrical communication with an RF energy source. The electrical spring contact is in electrical communication with the RF energy source.

In yet another embodiment, the support member includes a shroud and an attachment portion. At least a portion of the shroud is extendable from the housing. At least a portion of the electrode assembly is extendable through the shroud. The attachment portion can include a cavity in communication with the inert gas source. The shroud is configured for receipt of the attachment portion. The inert gas source is desirably in communication with the electrode assembly and the support member. The seal preferably comprises an O ring seal formed about the shroud. At least a portion of the support member is fabricated from silicone or a similar heat resistant material suitable for electrosurgery.

BRIEF DESCRIPTION OF THE DRAWINGS

Various embodiments of the present disclosure are described herein, with reference to the drawings wherein:

FIG. 2 is a side view of the apparatus shown in FIG. 1 with a left half of a housing removed;

FIG. 3 is a side view of the left half of the housing shown in FIG. 1;

FIG. 4 is an enlarged cut-away view of a distal end of the left half shown in FIG. 3;

FIG. 5 is a side view of a right half of the housing shown in FIG. 1;

FIG. 10 is an enlarged perspective view of an electrode assembly shown in FIG. 2;

FIG. 11 is a side view, in part cross-section, of the electrode assembly shown in FIG. 10;

DETAILED DESCRIPTION OF THE EXEMPLARY EMBODIMENTS

The embodiments of the apparatus and methods disclosed herein are discussed in terms of procedures for thermally treating tissue and related instrumentation. It is contemplated that the present apparatus and methods find application in both open and minimally invasive procedures including endoscopic and laparoscopic procedures wherein access to the surgical site is achieved through a cannula, small incision, or a naturally occurring orifice.

In the discussion which follows, the term proximal, as is traditional, will refer to the portion of the structure which is closer to the operator, and the term distal, will refer to the portion which is further from the operator.

Figure 1:
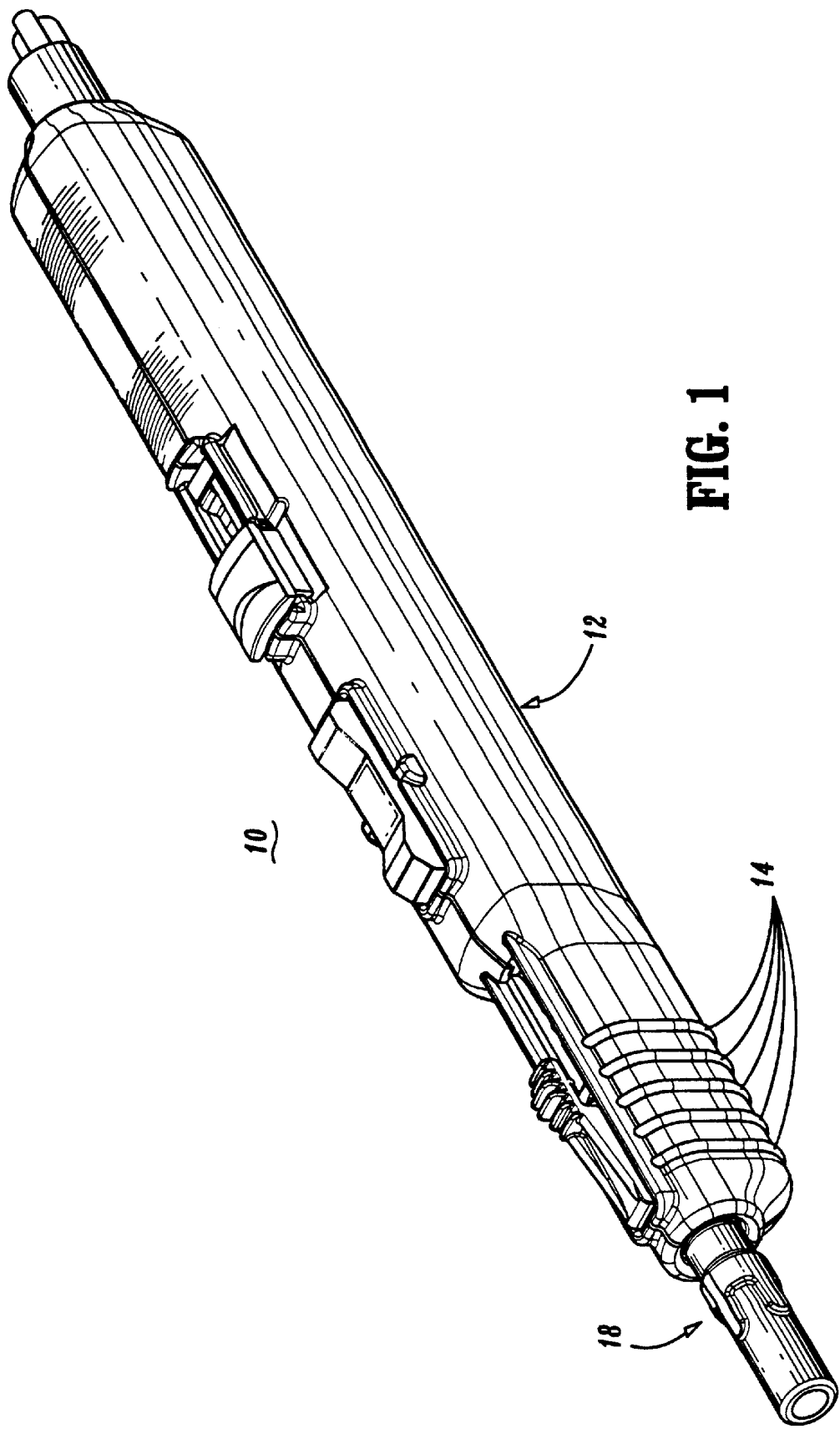
FIG. 1 is a perspective view of one embodiment of an inert gas enhanced electrosurgical apparatus in accordance with the present disclosure.

In accordance with the present disclosure, referring now in detail to the drawings wherein like reference numerals identify similar or like components throughout the several views, FIG. 1 illustrates one embodiment of an inert gas enhanced electrosurgical apparatus in accordance with the principles of the present disclosure. Inert gas enhanced electrosurgical apparatus 10 includes a housing 12 having ridges 14 formed therein projecting from an inner surface thereof. A support member 18 is also included having a portion thereof being disposed within housing 12. Electrosurgical apparatus 10 can be assembled to form a seal about an electrode and a gas tube, discussed below, without the need for additional manufacturing processes to create the seal. The electrosurgical apparatus described herein comprises an electrosurgical pencil-type instrumentation connected to an RF energy source. It is contemplated that the electrosurgical apparatus may also be suitably used with other surgical devices such as, for example, remote controlled surgical units or robotic-type surgical units, laser surgical units, etc.

Referring to FIG. 2, an electrode assembly 16 has a portion thereof disposed within housing 12. Support member 18 is disposed about a distal portion of electrode assembly 16. Ridges 14 of housing 12 are engageable with support member 18 such that a fluid tight seal is formed therewith. Support member 18 forms a fluid tight seal with the electrode by an interference fit which allows adjustment of electrode assembly 16. Support member 18 also forms a fluid tight seal about a gas tube assembly, discussed below.

The above mentioned seals of electrosurgical apparatus 10, as will be discussed in greater detail below, are advantageously formed and retain the components of electrosurgical apparatus 10 without the need for additional manufacturing processes such as, for example, welding, gluing, adhesives, etc. The seals created by engagement of the described portions of apparatus 10 are formed by interference fit. The interference fit includes engaging contact of the portions that prevent fluid leakage, as will be discussed below. It is contemplated that sealing engagement may alternatively include friction fit, pressure fit, etc.

Housing 12 is elongated and can be fabricated from materials suitable for electrosurgery, such as, for example, aluminum, stainless steel, and/or polymerics. Housing 12 can be constructed from a sterilizable material and may be disposable. In the event that a metallic material is used for construction, those portions of housing 12 should be properly insulated as necessary from electrical components disposed therein to prevent potential injury to a user or malfunction of the apparatus.

Referring to FIGS. 3–5, housing 12 has a first portion 20 and a second portion 22 that define a cavity 24 therebetween. First portion 20 comprises a left section of housing 12. Second portion 22 comprises a right section of housing 12. Housing 12 is substantially tubular for retaining the components of electrosurgical apparatus 10. Portions 20 and 22 are substantially rectangular. It is contemplated that housing 12 and portions thereof may be alternatively configured for various surgical applications or the particular preference of a user. It is further contemplated that portions of housing 12 may be monolithically formed using known fabrication techniques.

First portion 20 and second portion 22 comprise interlocking halves. First portion 20 includes a recessed border 26 (FIG. 3) that receives and is cooperatively engaged by a raised border 28 (FIG. 5) of second portion 22. Recessed border 26 is formed about the periphery of first portion 20. Raised border 28 is similarly and correspondingly formed about the periphery of second portion 22. Borders 26 and 28 interlock to maintain housing 12 and the components disposed therein in a locked relationship. It is contemplated that the borders may be snap fit, pressure fit, friction fit, etc. It is further contemplated that the borders may engage and be retained by external pressure, latch mechanisms, etc. It is envisioned that the borders may comprise only a portion of the periphery of the respective portions.

Referring to FIG. 4 which shows a distal end of first portion 20, housing 12 includes a first opening 30 adjacent a distal portion 32 thereof. First opening 30 is positioned on housing 12 to face a targeted surgical site. It is contemplated that first opening 30 may also be laterally formed on one or both of portions 20 and 22. First opening 30 is formed by assembly of first portion 20 and second portion 22 and is in communication with cavity 24 of housing 12. It is contemplated that first opening 30 may also be formed after assembly, such as, for example, by a hole punch, drill, etc. First opening 30 is circular and configured for receipt and disposal of support member 18 therein. It is envisioned that first opening 30 may be alternately configured, such as, for example, rectangular, elliptical, etc.

Figure 12:
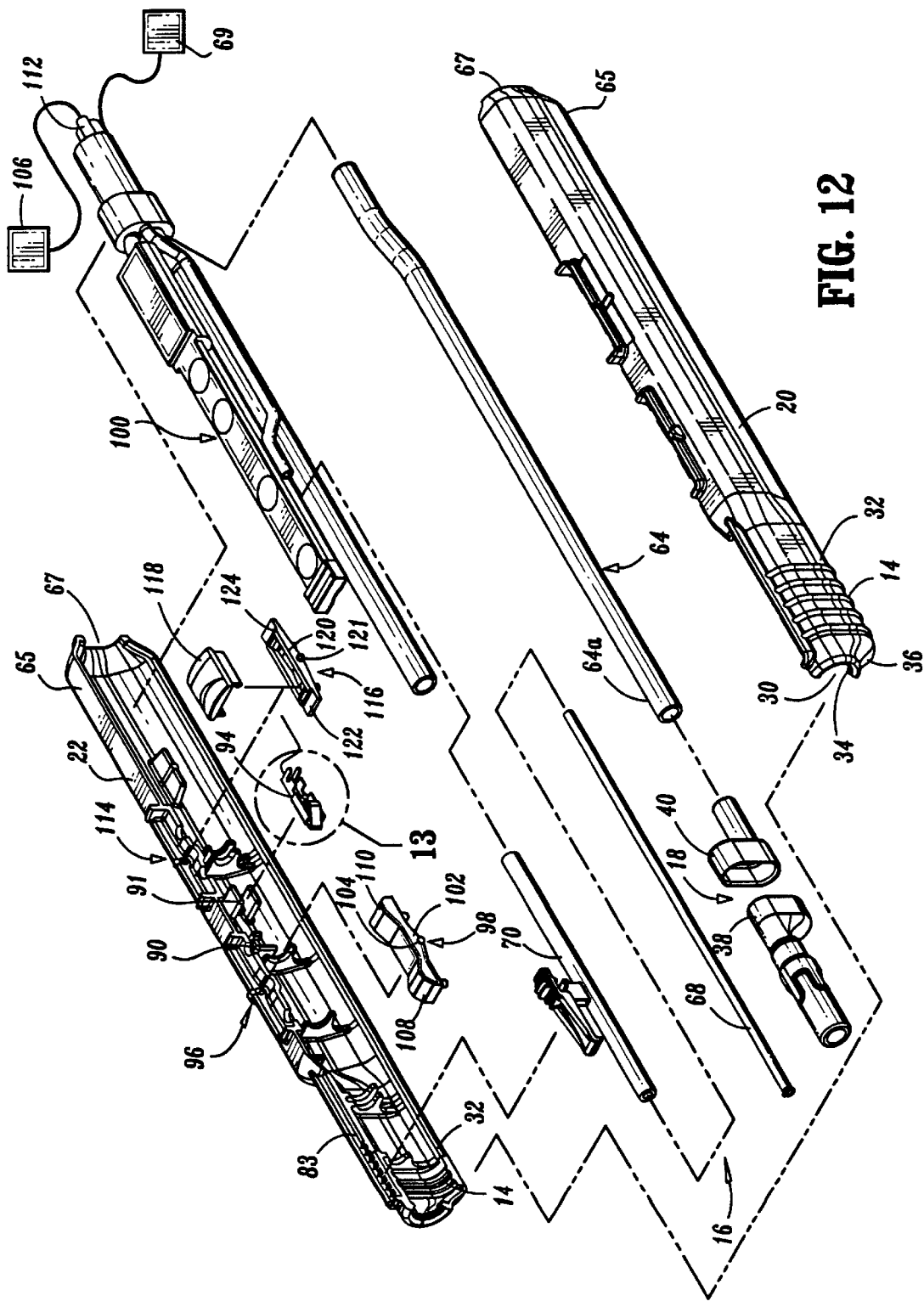
FIG. 12 is an exploded perspective view of the apparatus shown in FIG. 1.

First opening 30 includes an annular ring portion 34 which forms a fluid tight seal with support member 18. Referring to FIGS. 2 and 12, portion 36 of housing 12 adjacent first opening 30 is flexible and resilient so that, upon insertion of support member 18 within first opening 30, annular ring portion 34 is caused to outwardly flare. A seal is formed between support member 18 and annular ring portion 34 due to the interference fit created by insertion of support member 18 therein and the resilience of portion 36. The seal formed advantageously prevents leakage of gas about support member 18 and to the exterior of housing 12. It is contemplated that first opening 30 may have alternate configurations corresponding to the design of support member 18. It is further contemplated that the degree of flexibility of portion 36 may be altered for the particular surgical application according to the materials of construction of housing 12 and/or its configuration.

First portion 20 and second portion 22 include plurality of ridges 14 formed adjacent distal portion 32 of housing 12. Ridges 14 are oriented substantially orthogonal to a longitudinal axis A defined by housing 12 (FIGS. 2–5). It is contemplated that a single or multiple ridges may be formed with housing 12. It is further contemplated that ridges 14 may be formed at various angular orientations relative to longitudinal axis A depending on the sealing engagement desired and/or the configuration and orientation of support member 18 within housing 12.

Ridges 14 are formed monolithically with housing 12 by known fabrication techniques. It is contemplated that ridges 14 may be integrally connected within housing 12 by, such as, for example, an insert, etc. Ridges 14 project into cavity 24 of housing 12. Housing 12, adjacent ridges 14, is flexible and resilient so that, upon assembly of housing 12 with support member 18, ridges 14 are caused to resiliently flex about support member 18.

An O-ring fluid tight seal is formed between ridges 14 and an outer surface of support member 18 due to the interference fit created by assembly of housing 12 and correspondingly, support member 18 with ridges 14. Ridges 14 form a tubular configuration with cavity 24 for receipt of support member 18. It is contemplated that ridges 14 may form alternate configurations corresponding to the configuration of support member 18. The O-ring seal formed advantageously prevents leakage of gas about support member 18 and the components of electrosurgical apparatus 10 disposed therein. It is contemplated that the flexibility of ridges 14 may be altered for the particular surgical application according to the materials of construction of housing 12 and/or its configuration adjacent ridges 14.

Support member 18 includes a shroud 38 and an attachment portion 40. The components of support member 18 are fabricated from silicone. It is contemplated that other materials having heat-resistant characteristics to reduce, for example, eschar buildup, and which are suitable for electrosurgical applications may alternatively be used.

Figure 6:
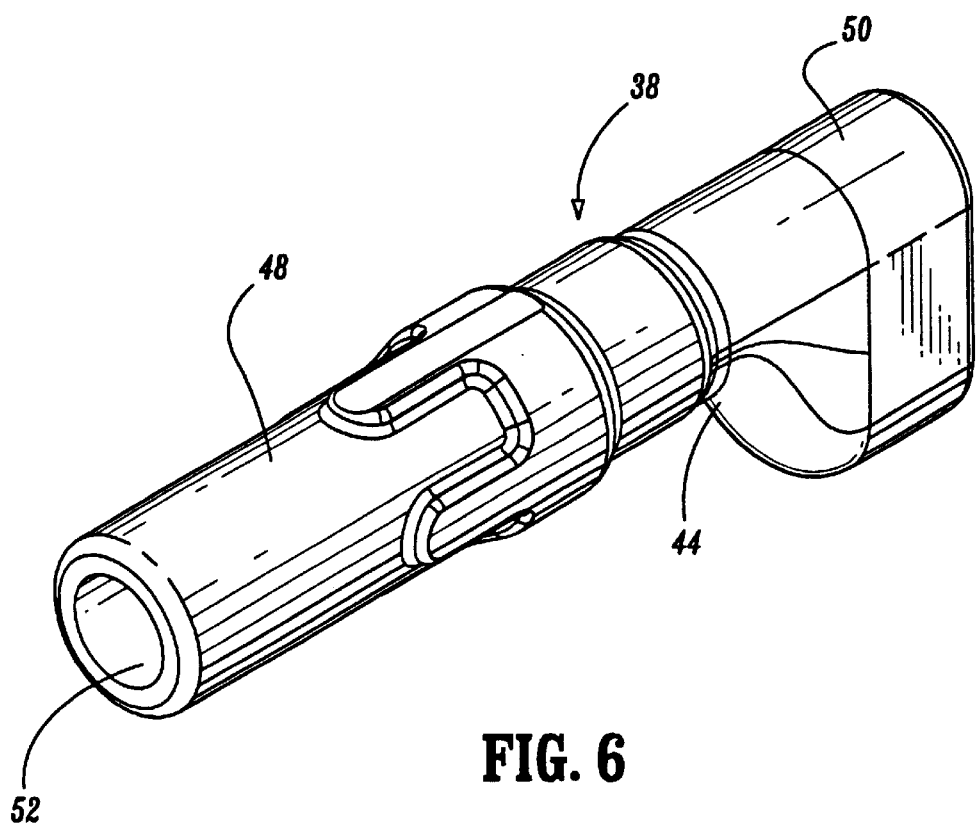
FIG. 6 is an enlarged perspective view of a shroud of a support member shown in FIG. 1.
Figure 7:
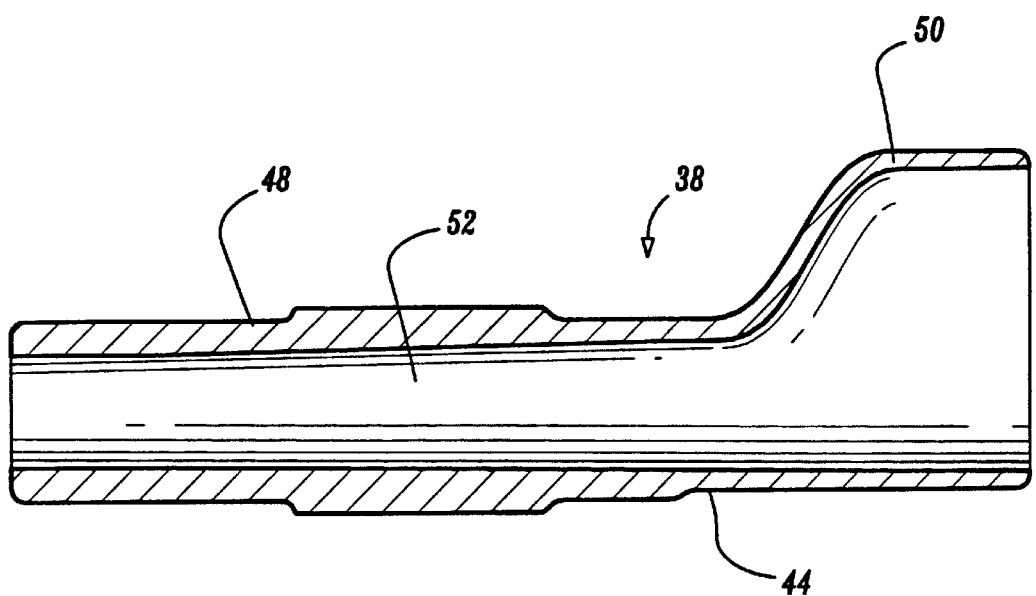
FIG. 7 is a side cross-sectional view of the shroud shown in FIG. 6.

Referring to FIGS. 6 and 7, an outer surface 44 of shroud 38 is configured for engaging annular ring portion 34 of first opening 30 to form the fluid tight seal, as discussed above, with regard to FIG. 4. Shroud 38 has a funnel-like configuration and includes an elongated portion 48 and a connector portion 50. Elongated portion 48 is extendable through first opening 30 of housing 12. Elongated portion 48 defines an inner cavity 52 whereby a distal portion of electrode assembly 16 is disposed.

Shroud 38 is monolithically formed by known fabrication techniques and inner cavity 52 of elongated portion 48 is telescopically configured for passage of gas therethrough, thereby delivering electrosurgical energy via the electrically charged stream of inert gas as electrode assembly 16 is activated. Connector portion 50 of shroud 38 is substantially tubular and received by attachment portion 40 in a fluid tight sealing engagement, as shown in FIGS. 2 and 12. The fluid tight sealing engagement may be formed by interference fit, friction fit, etc. It is contemplated that shroud 38 and attachment portion 40 of support member 18 may be monolithically formed by known fabrication techniques. Gas is fed through connector portion 50 and delivered through elongated portion 48 about electrode assembly 16.

Figure 8:
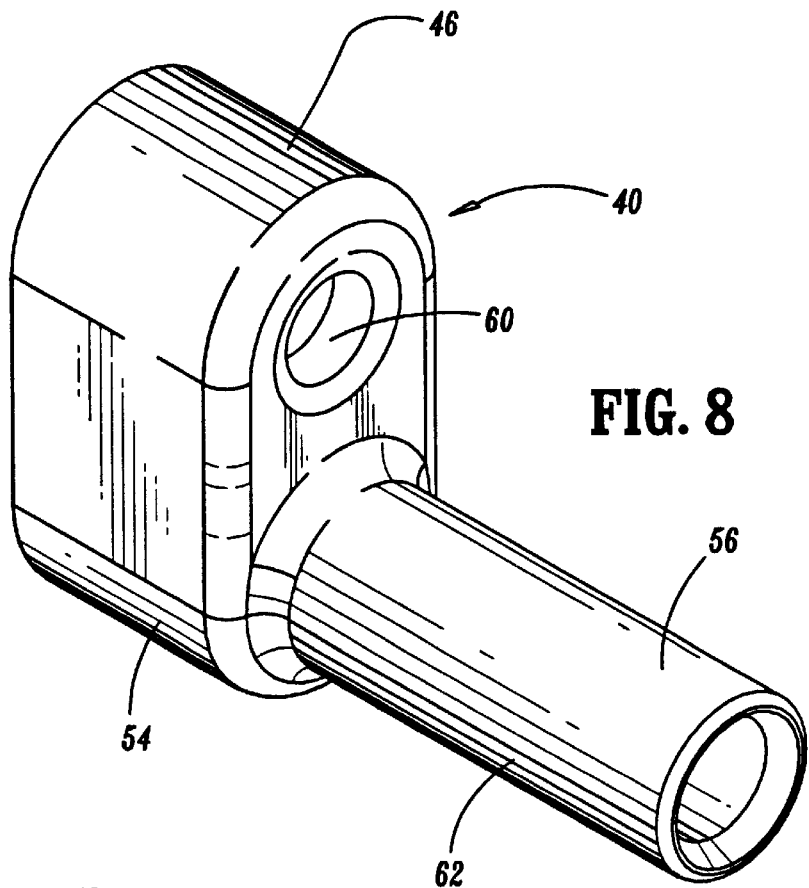
FIG. 8 is an enlarged perspective view of an attachment portion of the support member shown in FIG. 1.
Figure 9:
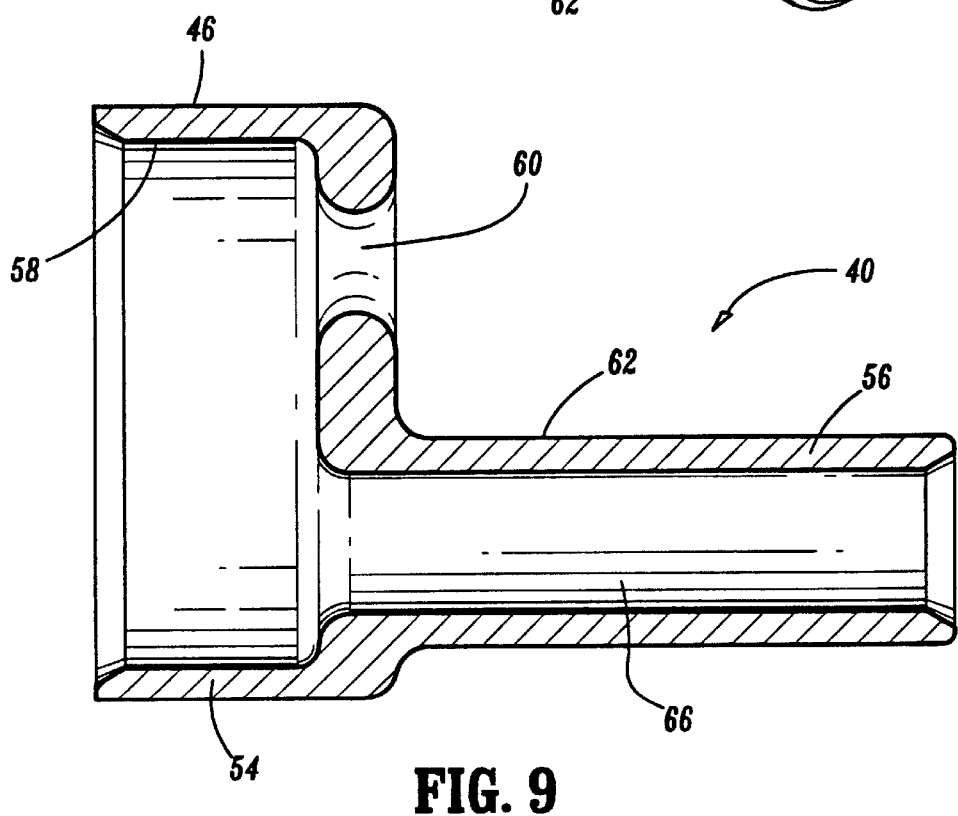
FIG. 9 is a side cross-sectional view, in part elevation, of the attachment portion shown in FIG. 8.

Referring to FIGS. 8 and 9, an outer surface 46 of attachment portion 40 is configured for engaging ridges 14 to form the fluid tight seal, as discussed above, with regard to FIG. 4. Attachment portion 40 includes an enclosure portion 54 and a connection portion 56. Enclosure portion 54 defines an inner surface 58 that engages connector portion 50 of shroud 38. Enclosure portion 54 receivably encloses shroud 38 in a fluid tight sealing engagement to prevent gas leakage, discussed above with regard to FIGS. 6 and 7, and facilitate connection to an appropriate inert gas source, discussed below.

Enclosure portion 54 defines an opening 60 whereby a portion of electrode assembly 16 is disposed therein and in a fluid tight sealing engagement, which will be discussed below with regard to FIGS. 10 and 11. Opening 60 is substantially aligned with cavity 52 of shroud 38 for proper alignment of electrode assembly 16 within support member 18.

Connection portion 56 extends proximally within housing 12 from enclosure portion 54. Connection portion 56 includes an outer surface 62 which engages a gas connector 64a of gas tube assembly 64, as shown in FIGS. 2 and 12, to form a fluid tight seal therewith. The fluid tight seal may be formed by interference fit, friction fit, etc. It is contemplated that connection portion 56 may be monolithically formed with gas connector 64a by known fabrication techniques. The fluid tight seal facilitates communication of a cavity 66, defined by connection portion 56, and gas tube assembly 64.

Gas tube assembly 64 extends from connection portion 56 to a proximal portion 65 of housing 12. Gas tube assembly 64 extends through housing 12 and through a second opening 67 defined adjacent proximal portion 65. Second opening 67 is formed by assembly of first portion 20 and second portion 22 and is in communication with cavity 24 of housing 12. It is contemplated that second opening 67 may also be formed after assembly, such as, for example, by a hole punch, drill, etc. Second opening 67 is circular and configured for receipt and disposal of portions of electrode assembly 16 and gas tube assembly 64. It is contemplated that second opening 67 may be alternatively configured for receipt of the portions of electrosurgical apparatus 10 disposed therein. Gas tube assembly 64 is in communication with an inert gas source 69.

Referring to FIGS. 10–12, electrode assembly 16 includes an electrode 68 and an adjustment assembly 70. Electrode 68 is elongated and tubular, and is fabricated from an electrically conductive material, such as, for example, tungsten, stainless steel, etc., that is suitable for electrosurgical applications. Electrode 68 is configured for passage of inert gas thereabout and therethrough a cavity 72 defined therein.

Electrode 68 is movably disposed within cavity 24 of housing 12. A distal portion 74 of electrode 68 is received by support member 18 for communicating with gas tube assembly 64. Distal portion 74 is received by support member 18 and forms a fluid tight seal with support member 18 by an interference fit created therewith.

Electrode 68 engages opening 60 (FIGS. 8 and 9) of attachment portion 40 to form the fluid tight seal therewith. Electrode 68 includes a flared end 76 which is pressure fit or "popped" into attachment portion 40 to form the interference fit with opening 60 and an outer surface of the shaft of electrode 68. Gas is thereby prevented from leaking into housing 12 and electrode adjustment, using adjustment assembly 70 discussed below, is facilitated to control the electrically charged stream of electrosurgical energy being delivered.

Distal portion 74 of electrode 68 is disposed within support member 18. Electrode 68 includes slots 78 that facilitate passage of gas through and about the electrode. As gas is delivered from gas tube assembly 64 within attachment portion 40, it is directed through support member 18. Inert gas flows through slots 78 and about energized electrode 68 delivering electrosurgical energy via the electrically charged stream of inert gas through shroud 38 to a targeted surgical site.

Adjustment assembly 70 of electrode assembly 16 engages housing 12 for incrementally adjusting an amount of movement of electrode 68 relative to housing 12. Adjustment assembly 70 has a shaft portion 71 coaxially disposed about the shaft of electrode 68. The adjustment assembly 70 is molded from a polymeric material using known fabrication techniques. It is contemplated that other materials may be used such as, for example, aluminum, steel, etc.

Adjustment assembly 70 is mounted to electrode 68 by adhesive or the like. It is contemplated that shaft portion 71 may also be mounted to the electrode by friction fit, etc. Due to the assembly of electrode 68 and shaft portion 71, movement of adjustment assembly 70 causes corresponding movement of electrode 68. Engagement of adjustment assembly 70 with housing 12 results in a uniform linear actuation of electrode 68 for adjusting depth thereof and controlling the stream of electrosurgical energy being delivered to a targeted surgical site, as will be discussed below.

Adjustment assembly 70 includes a neck member 80 extending from shaft portion 71 and a cantilever member 82 connected thereto. Cantilever member 82 includes a button 84 that is depressable for manipulating a notch end 86 of cantilever member 82 upwards and downwards to engage housing 12 for incremental adjustment of electrode 68. Cantilever member 82 is pivotal relative to neck member 80. Pivotal movement is facilitated by a flexible and resilient junction 81. Pivoting of the cantilever member may also be facilitated by a hinge, bracket, etc.

Referring to FIG. 2, notch end 86 is configured to engage wedge projections 88 defined by housing 12. Depth of electrode 68 within support member 18 is adjusted by manipulating button 84 to raise notch end 86 out of engagement with wedge projections 88. While continuing to depress button 84, adjustment assembly 70 is manipulated so that neck member 80 moves linearly along axis A within a slot 83 of housing 12. Manipulation of adjustment assembly 70 causes corresponding movement of electrode 68 within housing 12 along axis A for adjustment to the desired depth of electrode 68 within support member 18 according to the particular surgical application or preference of the user. The adjustment of the depth of electrode 68 allows the user to adjust and control the stream of electrosurgical energy being delivered through shroud 38. The energized stream of inert gas may be controlled to adjust intensity, thickness, etc. of the stream.

Once a desired depth of electrode 68 within support member 18 is reached, button 84 is released causing notch end 86 to pivot relative to neck member 80 by junction 81 and engage housing 12 between adjacent wedge projections 88. Electrode 68 remains fixed at the desired depth due to the engagement of notch end 86 between the particular wedge projections 88. It is contemplated that notch end 86 may engage a flat surface on housing 12 for adjustment of electrode 68 by a friction fit to maintain positioning of electrode 68. Further adjustments of the depth of electrode 68 can be made by further manipulations of adjustment assembly 70 according to the requirements of a particular surgical application and/or preference of the user.

Figure 13:
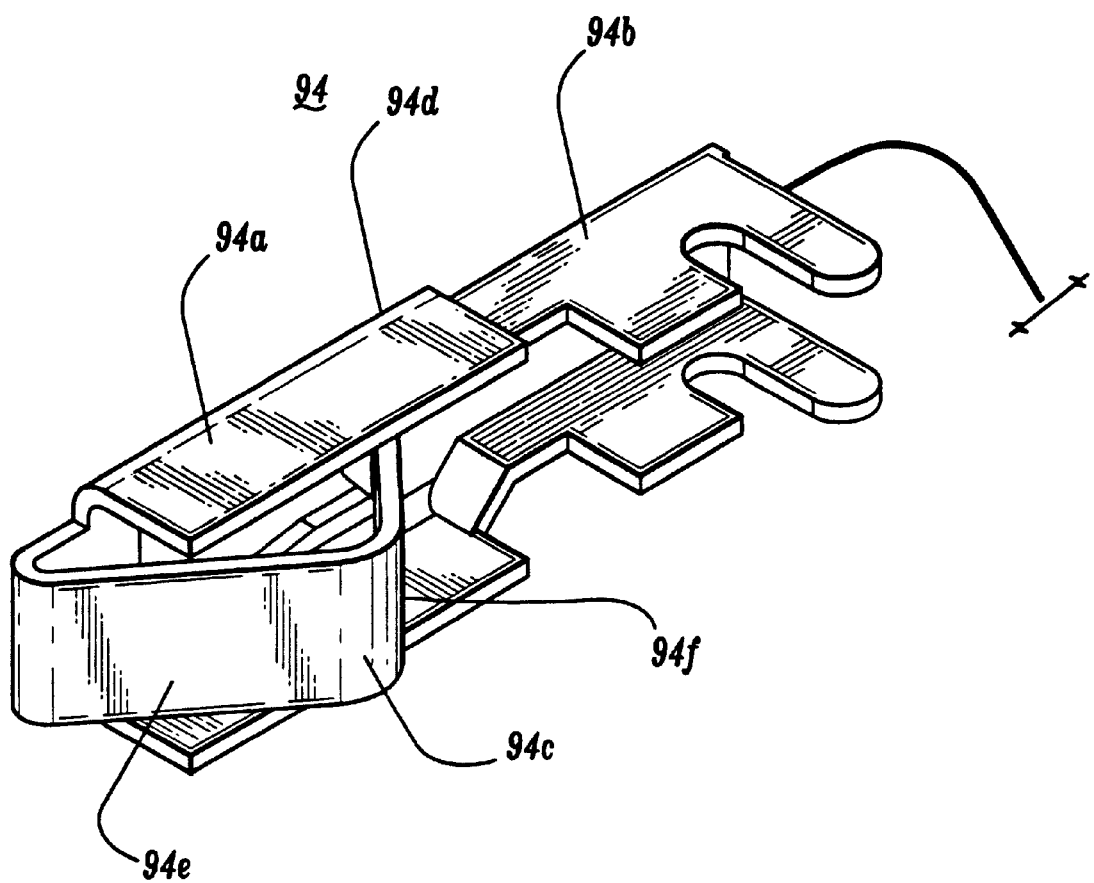
FIG. 13 is an enlarged perspective view of an electrical spring contact as shown in the indicated area of detail of FIG. 12.

Referring to FIG. 5, second portion 22 of housing 12 includes ribs 90 and 91 formed on an inner surface 92 thereof that project into cavity 24. Referring to FIGS. 12 and 13, ribs 90 and 91 are configured to engage and support an electrical spring contact 94 disposed within housing 12. Ribs 90 and 91 are monolithically formed with housing 12 and oriented substantially perpendicular to each other to facilitate support of electrical spring contact 94. It is contemplated that the ribs may be integrally connected to the housing. It is further contemplated that a single rib or a plurality of ribs may be used to support the electrical spring contact.

A first end 94a of electrical spring contact 94 is mounted onto ribs 90. A second end 94b is received and supported by ribs 91. A contact portion 94c of electrical spring contact 94 is configured to engage electrode assembly 16. Contact portion 94c resiliently extends from contact 94 so that, upon engagement with electrode assembly 16, electrode 68 is brought into electrical communication with an RF energy source, discussed below.

Contact portion 94c comprises a resilient arm extending from a body portion 94d of electrical spring contact 94. Contact portion 94c includes an insulative portion 94e directly attached to body portion 94d and a conductive portion 94f, extending from insulative portion 94e, which is resiliently engageable with body portion 94d. Insulative portion 94e maintains an open circuit between electrode 68 and the RF energy source, although electrode 68 may be engaging contact portion 94c.

To close the circuit between electrode 68 and the RF energy source, pressure is applied to housing 12, ribs 90 and 91 are caused to engagingly contact electrical spring contact 94. Correspondingly, electrical spring contact 94 engages electrode 68 causing conductive portion 94f to engagingly contact body portion 94d which in turn closes the circuit and establishes electrical communication between electrode 68 and the RF energy source via power source activator 96.

Referring to FIGS. 2 and 12, power source activator 96 includes a switch assembly 98 and is in communication with a circuitry assembly 100. Switch assembly 98 includes a handswitch 102 mounted to an outer surface of housing 12. Handswitch 102 pivots about a rocking pin 104 for activating an RF energy source 106 which is in electrical communication with power source activator 96 via circuitry assembly 100. Power source activator 96 is in electrical communication with electrical spring contact 94, as discussed above. When ribs 90 are pressed, switch assembly 98 is in electrical communication with electrode 68 for supplying electrode 68 with RF energy from RF energy source 106.

A distal portion 108 of handswitch 102 is depressed to activate a first specification for cutting, of which a portion of housing 12 adjacent distal portion 108 is suitably marked "CUT". Alternatively, a proximal portion 110 of handswitch 102 is depressed to activate a second specification for coagulation, of which a portion of housing 12 adjacent proximal portion 110 is suitably marked "COAG". Handswitch 102 alternatively activates both types of RF energy.

Handswitch assembly 98 is in electrical communication with RF energy source 106 via wiring 112 of circuitry assembly 100. Wiring 112 provides an electrical connection to RF energy source 106 which is suitable for electrosurgical applications as is known to one skilled in the art. Circuitry assembly 100 further includes and/or is connected to any suitable digital computer or microprocessor having the appropriate preprogrammed electronics and software required for operation thereof, as is known in the art. The particular electronic elements utilized can be readily assembled and operated by one skilled in the art in light of the description provided herein, therefore, further detailed explanation of the specific electronics and programming is not provided herein. The circuitry assembly may be configured to monitor and control surgical conditions relating to electrosurgical apparatus 10 for delivering the stream of electrosurgical energy via the electrically charged stream of inert gas to a targeted surgical site.

An inert gas activator 114 includes a handswitch 116 and is in communication with circuitry assembly 100. Handswitch 116 is mounted to an outer surface of housing 12 adjacent handswitch 102 of switch assembly 98. Handswitch 116 includes a tab 118. Tab 118 is mounted to a rail 120 for slidable linear movement in both proximal and distal directions along axis A. Rail 120 pivots about a pin 121 which allows rail 120 in cooperation with tab 118 to activate or prevent delivery of inert gas from inert gas source 69 and through gas tube assembly 64. It is contemplated that power source activator 96 may activate the supply of RF energy from RF energy source 106 to perform cutting or coagulation at a targeted surgical site with or without inert gas enhancement of electrosurgical apparatus 10 during electrosurgery.

Tab 118 is slidably manipulated to a distal portion 122 of handswitch 116 to activate delivery of inert gas from inert gas source 69, whereby a portion of housing 12 adjacent distal portion 122 is suitably marked "Ar". In the distal position, tab 118 communicates with a portion of circuitry assembly 100 which sends an activation signal to inert gas source 69. Alternatively, tab 118 is slidably manipulated to a proximal portion 124 of handswitch 116 to prevent delivery of inert gas from inert gas source 69, whereby a portion of housing 12 adjacent proximal portion 124 is suitably marked "Ar". In position, tab 118 communicates with a portion of circuitry assembly 100 which sends a prevent signal to inert gas source 69. Handswitch 116 alternatively activates and prevents delivery of inert gas from inert gas source 69.

Inert gas activator 114 electronically controls delivery of inert gas from inert gas source 69 via circuitry assembly 100. Circuitry assembly 100 includes and/or is connected to a digital computer or microprocessor, as discussed above. Circuitry assembly 100 in cooperation with inert gas activator 114 controls and monitors the supply of inert gas, as is known to one skilled in the art in light of the description provided herein.

In operation, inert gas enhanced electrosurgical apparatus 10 is assembled in light of the description provided herein to form fluid tight seals between support member 18 and housing 12, and support member 18 and electrode assembly 16. Electrosurgical apparatus 10 is appropriately connected to RF energy source 106 and inert gas source 69. During electrosurgery, electrosurgical apparatus 10 is appropriately sterilized according to the particular application.

Electrosurgical apparatus 10 is manipulated so that shroud 38 is positioned adjacent a targeted surgical site. Electrode 68 is adjusted to a desired depth to control the energized stream of inert gas via adjustment assembly 70, as discussed above, according to the particular surgical application or preference of the user. Power source activator 96 is manipulated for cutting or coagulation, as discussed above. Inert gas activator 114 is manipulated in cooperation with power source activator 96 to deliver an energized stream of inert gas to the targeted surgical site. It is contemplated that electrosurgical apparatus 10 may perform cutting and coagulation with or without inert gas enhancement.

It will be understood that various modifications may be made to the embodiments disclosed herein. For example, while specific embodiments of the apparatus have been described in detail, structures that perform substantially the same function in substantially the same way to achieve the same result may also be used. Therefore, the above description should not be construed as limiting but exemplifications of the various embodiments. One skilled in the art will envision other modifications within the scope and spirit of the claims appended hereto.

What is claimed is:

1. An inert gas enhanced electrosurgical apparatus comprising:
    a housing having at least one ridge formed therein;
    an electrode assembly having at least a portion thereof being disposed within the housing; and
    a support member having at least a portion thereof being disposed within the housing and about at least a portion of the electrode assembly, the at least one ridge of the housing being engageable with the support member such that a seal is formed therebetween.

2. An apparatus as recited in claim 1, wherein the housing includes a first portion and a second portion that define a cavity therebetween.

3. An apparatus as recited in claim 2, wherein the first and second portions comprise interlocking halves.

4. An apparatus as recited in claim 1, wherein the housing includes a first opening adjacent a distal portion of the housing and a second opening adjacent a proximal portion of the housing.

5. An apparatus as recited in claim 1, wherein the housing includes a plurality of ridges formed adjacent a distal portion of the housing.

6. An apparatus as recited in claim 1, wherein the at least one ridge is oriented substantially orthogonal to a longitudinal axis defined by the housing.

7. An apparatus as recited in claim 1, further comprising ribs formed on an inner surface of the housing.

8. An apparatus as recited in claim 7, wherein the ribs are oriented substantially orthogonal to a longitudinal axis of the housing.

9. An apparatus as recited in claim 2, wherein the first and second portions include ribs formed therein which are oriented substantially orthogonal to a longitudinal axis of the housing.

10. An apparatus as recited in claim 1, further comprising wedge projections disposed on an outer surface of the housing, wherein the electrode assembly includes an adjustment assembly coaxially disposed about an outer surface of the electrode assembly including a neck member that engages the wedge projections of the housing for incrementally adjusting an amount of movement of the electrode assembly relative to the housing.

11. An apparatus as recited in claim 1, further including an inert gas activator mounted to the housing and in communication with an inert gas source.

12. An apparatus as recited in claim 1, further including a power source activator mounted to the housing and in electrical communication with an RF power source.

13. An apparatus as recited in claim 7, further comprising an electrical spring contact being disposed within the housing and configured to cooperate with the ribs to facilitate electrical communication with the electrode assembly.

14. An apparatus as recited in claim 13, wherein the electrical spring contact is in direct electrical communication with an RF power source.

15. An apparatus as recited in claim 1, wherein the support member includes a shroud and an attachment portion.

16. An apparatus as recited in claim 1, wherein the support member is mounted adjacent a distal portion of the housing.

17. An apparatus as recited in claim 15, wherein at least a portion of the shroud is extendable from the housing.

18. An apparatus as recited in claim 15, wherein at least a portion of the electrode assembly is extendable through the shroud.

19. An apparatus as recited in claim 15, wherein the attachment portion includes a cavity in communication with an inert gas source.

20. An apparatus as recited in claim 15, wherein the shroud is configured for receipt of the attachment portion.

21. An apparatus as recited in claim 1, further including an inert gas source being in communication with the electrode assembly and the support member.

22. An apparatus as recited in claim 15, wherein the seal comprises an O ring seal formed about the shroud.

23. An inert gas enhanced electrosurgical apparatus comprising:
a housing having ribs formed therein;
an electrode assembly having at least a portion thereof being disposed within the housing;
an electrical spring contact being disposed within the housing and configured to cooperate with the ribs of the housing to facilitate electrical communication with the electrode assembly;
a support member having at least a portion thereof disposed within the housing about at least a portion of the electrode assembly, the housing including ridges therein which are engageable with the support member such that a seal is formed therebetween.

24. An apparatus as recited in claim 23, wherein the housing includes a first portion and a second portion that define a cavity therebetween.

25. An apparatus as recited in claim 24, wherein the first and second portions comprise interlocking halves.

26. An apparatus as recited in claim 23, wherein the housing includes a first opening adjacent a distal portion of the housing and a second opening adjacent a proximal portion of the housing.

27. An apparatus as recited in claim 23, wherein the ribs are oriented substantially orthogonal to a longitudinal axis of the housing.

28. An apparatus as recited in claim 23, further comprising wedge projections disposed on an outer surface of the housing, wherein the electrode assembly includes an adjustment assembly coaxially disposed about an outer surface of the electrode assembly and including a neck member that engages the wedge projections of the housing for incrementally adjusting an amount of movement of the electrode assembly relative to the housing.

29. An apparatus as recited in claim 23, wherein the electrical spring contact is in direct electrical communication with an RF power source.

30. An apparatus as recited in claim 23, wherein the support member includes a shroud and an attachment portion.

31. An apparatus as recited in claim 30, wherein the attachment portion includes a cavity in communication with an inert gas source.

32. An apparatus as recited in claim 23, further including an inert gas source being in communication with the electrode assembly and the support member.

33. An apparatus as recited in claim 30, wherein the seal comprises an O ring seal formed about the shroud.

34. An inert gas enhanced electrosurgical apparatus comprising:
an elongated tubular housing having a first portion and a second portion that define a cavity therebetween, the housing including a first opening adjacent a distal portion thereof and a second opening adjacent a proximal portion thereof, the first and second portions including a plurality of ridges formed adjacent the distal portion of the housing and being oriented substantially orthogonal to a longitudinal axis defined by the housing, the first and second portions further including ribs formed therein oriented substantially orthogonal to the longitudinal axis, the housing further including wedge projections, an inert gas activator and a power source activator being disposed on an outer surface of the housing;
an elongated tubular electrode configured for passage of inert gas thereabout and therethrough a cavity defined therein, the electrode being movably disposed within the cavity of the housing, a distal portion of the electrode being extendable through the first opening of the housing, the electrode including an adjustment assembly coaxially disposed about an outer surface of the electrode, the adjustment assembly including a neck member that engages the wedge projections of the housing for incrementally adjusting an amount of movement of the electrode relative to the housing;
an electrical spring contact being mounted within the housing and in electrical communication with the power source activator, the electrical spring contact being configured to cooperate with the ribs of the housing for electrically communicating with the electrode;
an RF power source in electrical communication with the electrode and the power source activator;
a support member including a silicone shroud and an attachment portion, the support member being mounted adjacent a distal portion of the housing and being projectable from the first opening of the housing, wherein at least a portion of the electrode is projectable through the shroud, the attachment portion including a cavity configured for passage of inert gas therethrough, the shroud being configured for receipt of the attachment portion; and
an inert gas source being in communication with the electrode and the support member.

* * * * *